United States Patent [19]
Shiratsuchi et al.

[11] 4,448,989
[45] May 15, 1984

[54] N-NITROXYALKYLENE BENZAMIDE DERIVATIVES

[75] Inventors: Masami Shiratsuchi, Musashimurayama; Hiroshi Ishihama, Higashimurayama; Yasumi Uchida, Ichikawa, all of Japan

[73] Assignee: Kowa Company, Ltd., Japan

[21] Appl. No.: 451,322

[22] Filed: Dec. 20, 1982

[30] Foreign Application Priority Data

Dec. 24, 1981 [JP] Japan ................................ 56-208105

[51] Int. Cl.$^3$ ................. C07C 103/76; C07C 103/78; A61K 31/165
[52] U.S. Cl. ..................................... 564/165; 424/324
[58] Field of Search ......................... 564/165; 424/324

[56] References Cited
U.S. PATENT DOCUMENTS
4,374,840 2/1983 Shiratsuchi et al. ............ 564/165 X FOREIGN PATENT DOCUMENTS
1936693 1/1970 Fed. Rep. of Germany ...... 564/165
1392610 4/1975 United Kingdom ................ 564/165

Primary Examiner—Thomas A. Waltz
Attorney, Agent, or Firm—Wenderoth, Lind & Ponack

[57] ABSTRACT

A compound represented by the following formula

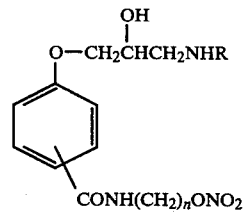

wherein R represents a lower alkyl group having 2 to 6 carbon atoms, and n is an integer of from 1 to 5.

4 Claims, No Drawings

N-NITROXYALKYLENE BENZAMIDE DERIVATIVES

This invention relates to novel benzamide derivatives which have various pharmacological activities and are useful in the pharmaceutical field.

More specifically, this invention pertains to a compound represented by the following formula (I)

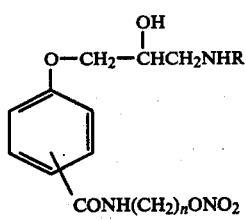

(I)

wherein R represents a lower alkyl group having 1 to 4 carbon atoms, and n is an integer of from 1 to 5.

Pharmaceutically useful aromatic aminoethanol compounds of the following formula (A) having various pharmacological activities have been disclosed by some workers partly including the present inventors in Japanese Laid-Open Patent Publication No. 113748/1981 (corresponding to European Patent Application Publication No. 0034461 (published Aug. 26, 1981); and U.S. patent application Ser. No. 233,643 filed Feb. 11, 1981).

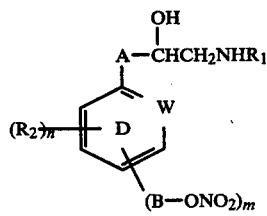

(A)

wherein
A represents a direct bond or the bond —O—CH$_2$—,
B represents a C$_1$–C$_{11}$ alkylene group bonded to a carbon atom of the aromatic ring D either directly or through —O—, —S—, —SO— or —NH—,
W represents a carbon or nitrogen atom,
R$_1$ represents a C$_3$–C$_7$ alkyl group, a hydroxy(C$_1$–C$_6$ alkyl) group, or a phenyl- or diphenylalkyl group with the alkyl group having 1 to 4 carbon atoms,
R$_2$ represents a member selected from the class consisting of hydrogen, halogen, OH, C$_1$–C$_4$ alkyl, NO$_2$, C$_1$–C$_4$ alkoxy, acetyl, allyloxy, carbamoyl and sulfamoyl, and when two or more R$_2$ groups exist, they may be identical or different, and n represents 1, 2 or 3 and m represents 1 or 2, provided that n+m≧4.

The present inventors made further investigations about benzamide derivatives and their synthesis and utilization. Consequently, they have succeeded in synthesizing the novel compounds of formula (I) which have not been described previously in the literature. It has also been found that these novel compounds have various pharmacological effects which make them useful for the treatment of cardiovascular diseases.

The compounds of formula (A) disclosed in the prior art are clearly distinguished from the compounds of the present invention in that the prior art compounds do not have the group —CONH(CH$_2$)$_n$ONO$_2$ shown in the above general formula (I).

The compounds of this invention have antihypertensive, vasodilating, β-blocking and blood flow increasing activities, and are useful as anti-anginal agents, antihypertensive agents, cerebral circulation improvers and antiarrhythmic agents.

It is an object of this invention therefore to provide novel compounds of general formula (I).

The above and other objects and advantages of the invention will become apparent from the following description.

The compounds (I) of this invention can be produced, for example, by the following processes.

Process (A)

A compound of the following formula (II)

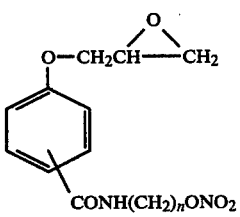

(II)

wherein n is the same as defined above,
is reacted with an amine of the following formula (III)

H$_2$NR   (III)

wherein R is the same as defined above.

Process (B)

A compound of the following formula (IV)

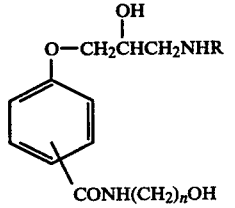

(IV)

wherein R and n are the same as defined above,
is subjected to a nitrate ester-forming reaction.

Process (C)

A compound of the following formula (VII)

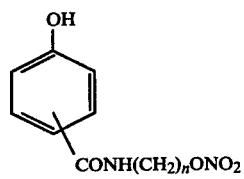

(VII)

wherein n is the same as defined above,
is subjected to an aminoalkanol-forming reaction.

Process (D)

A compound of the following formula (V)

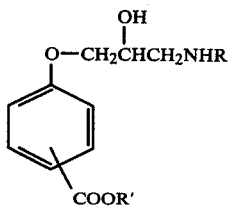

(V)

wherein R and R' are the same as defined above,
is reacted with a compound of the following formula (VI)

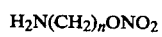

(VI)

wherein n is the same as defined above.

The compounds of formula (II), (IV), (V) and (VII) in processes (A), (B), (C) and (D) can, for example, be prepared from compounds of the following formula (VIII)

(VIII)

wherein R' represents hydrogen atom or a lower alkyl group,
by utilizing aminoalkanol-forming reaction, amination with a hydroxyalkylamine, nitrate ester-forming reaction, glycidyl-forming reaction, etc.

The following scheme shows several embodiments of producing the compound (I) of this invention including the production of the starting compounds (II), (IV), (V) and (VII) from the compound (VIII).

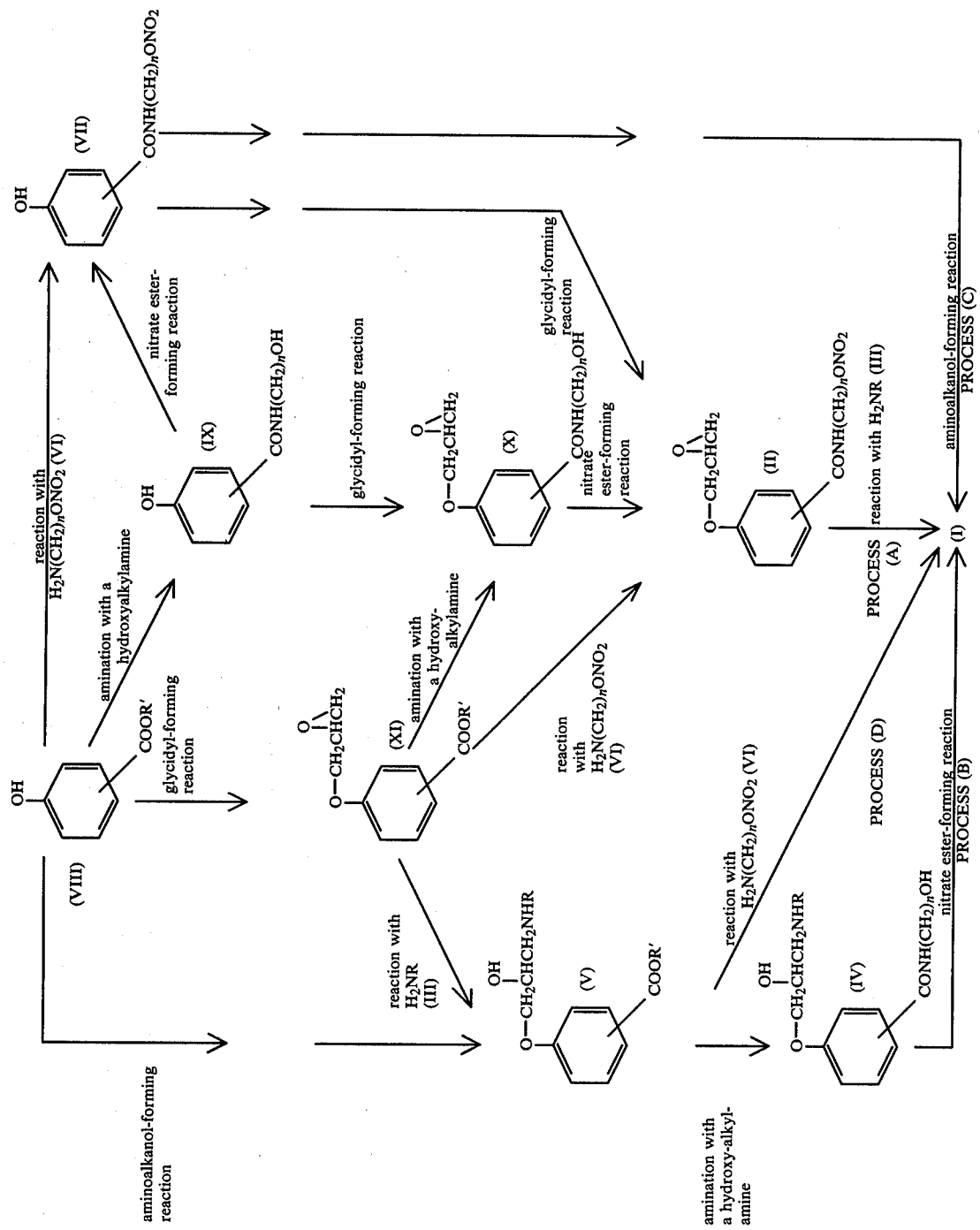

As is schematrically shown above, the compound of formula (II) used in process (A) can be obtained by subjecting the compound of formula (VIII) to a glycidyl-forming reaction, to amination with a hydroxyalkylamine of the formula $H_2N(CH_2)_nOH$ wherein n is the same as defined above and then to a nitrate ester-forming reaction, or by subjecting the compound of formula (VIII) to a glycidyl-forming reaction and then directly reacting it with a compound of formula (VI) $H_2N(CH_2)_nONO_2$ wherein n is the same as defined above. The compound of formula (II) can also be obtained by subjecting the compound of formula (VIII) to amination with the hydroxyalkylamine, to a glycidyl-forming reaction and then to a nitrate ester-forming reaction, or by reacting the compound of formula (VIII) with the compound of formula (VI) to form the compound of formula (VII) and then subjecting it to a glycidyl-forming reaction.

The compound of formula (V) used in process (D) can be obtained by subjecting the compound of formula (VIII) to a glycidyl-forming reaction and then reacting the resulting product with the compound of formula (III) $H_2NR$. The compound of formula (V) can also be obtained by directly subjecting the compound of formula (VIII) to an aminoalkanol-forming reaction. The compound of formula (IV) used in process (B) can be obtained by subjecting the compound of formula (V), which can be obtained as above, to amination with a hydroxyalkylamine of the formula $H_2N(CH_2)_nOH$. The compound of formula (VII) used in process (C) can be obtained by directly reacting the compound of formula (VIII) with the compound of formula (VI); or by first aminating the compound of formula (VIII) with the hydroxyalkylamine of the above formula and then subjecting the product to a nitrate ester-forming reaction.

The reaction with $H_2NR$ (III), the nitrate ester-forming reaction, the aminoalkanol-forming reaction, the reaction with $H_2N(CH_2)_nONO_2$ (VI), the amination with $H_2N(CH_2)_nOH$, and the glycidyl-forming reaction can be carried out as follows:

1. Reaction with $H_2NR$ (III)

Amination of the compound of formula (II) or (XI) having an epoxy group can be effected by reacting it with the alkylamine of formula (III) in an inert solvent at room temperature to about 90° C. for several minutes to 1 hour. The inert solvent may, for example, be methanol, ethanol, or isopropanol. The amounts of the compound of formula (III) relative to the compound of formula (II) or (XI) can be properly selected. For example, it is 1 to about 5 moles per mole of the compound of formula (II) or (XI).

2. Nitrate ester-forming reaction

The nitrate ester-forming reaction of the compounds of formulae (IV), (IX) and (X) can be carried out by contacting the compound of formula (IV), (IX) or (X) with a nitrate ester-forming reactant such as fuming nitric acid, or a mixture of it with acetic anhydride, or a mixture of fuming nitric acid and sulfuric acid at a relatively low temperature in the presence or absence of a solvent. For example, the reaction is carried out at a temperature of from about −40° C. to room temperature for about 1 minute to about 1 hour. Preferably, one of the hydroxyl groups of the compound of formula (IV) or (IX) is protected before subjecting it to the nitrate ester-forming reaction. Protection can be effected, for example, by chloroacetylation, dichloroacetylation and trichloroacetylation.

The solvent used in the above reaction is an inert organic solvent such as acetonitrile, dioxane or tetrahydrofuran.

The mole ratios of the reactants can be selected as desired. For example, the amount of the nitrate ester-forming reactant is 1 to about 2 moles per mole of the compound of formula (IV), (XI) or (X).

3. Aminoalkanol-forming reaction

The aminoalkanol-forming reaction of the compound of formula (VIII) or (VII) can be carried out by reacting it with an alkylaminoalkanol under ordinary conditions.

4. Reaction with $H_2N(CH_2)_nONO_2$

The reaction of the compound of formula (V), (VIII) or (XI) with $H_2N(CH_2)_nONO_2$ can be carried out by contacting it with $H_2N(CH_2)_nONO_2$ in an inert solvent such as tetrahydrofuran or dioxane, when R' in these formula represents a lower alkyl group. The reaction can be carried out, for example, at room temperature to about 130° C. for about 1 to about 6 hours. The amount of $H_2N(CH_2)_nONO_2$ relative to the compound of formula (V), (VIII) or (XI) can be properly selected. For example, it is 1 to about 2 moles per mole of the compound of formula (V), (VIII) or (XI). Where R' in the above formulae represents a hydrogen atom, the above reaction can be carried out by contacting the compound of formula (V), (VIII) or (XI) having a free carboxyl group with $H_2N(CH_2)_nONO_2$ in the same inert solvent as mentioned above in the presence of a coupling reagent such as dicyclohexyl carbodiimide (DCC) or carbonyldiimidazole at a relatively low temperature of, for example, about 0° to about 70° C. The reaction time can be properly chosen, and is, for example, about 0.5 to about 10 hours. The amount of $H_2N(CH_2)_nONO_2$ relative to the compound of formula (V), (VIII) or (XI) is the same as that described above with regard to the case of R' being a lower alkyl group. The amount of the coupling reagent used is, for example, 1 to 5 moles.

5. Amination with $H_2N(CH_2)_nOH$

This reaction is carried out by contacting the compound of formula (VIII) or (XI) with the hydroxyalkylamine at room temperature to about 130° C. for about 1 to about 10 hours. The amount of the hydroxyalkylamine is, for example, 1 to 10 moles per mole of the compound of formula (VIII) or (XI).

6. Glycidyl-forming reaction

The glycidyl-forming reaction of the compound of formula (VIII), (VII) or (IX) can be carried out, for example, by contacting it with epichlorohydrin and piperidine at a reaction temperature of room temperature to 100° C. for about 1 to about 5 hours. The amount of epichlorohydrin used is about 10 to about 100 moles, and the amount of piperidine used is about 0.1 to about 1 mole, both per mole of the compound of formula (VIII), (VII) or (IX).

The compound of formula (I) of this invention can be obtained by properly selecting the above processes. The compound of formula (I) which can be so obtained have various pharmacological activities including vascular smooth muscle relaxing action, adrenegic- and β-blocking action resulting in a reduction in heart beat rate, myocardial oxygen consumption reducing action, blook flow increasing action and blood pressure lowering action. Because of these pharmacological activities, these compounds are useful as medicines for the treatment of cardiovascular diseases, such as anti-anginal drugs, hypotensive agents, improvers for the cardiovascular system, and antiarrhythmic drugs.

A pharmaceutical composition may be provided by using the compound of this invention and a liquid or solid carrier or diluent.

Liquid or solid carriers or diluents which can be used in this invention may include excipients, binders, lubricants, emulsifiers, etc. known in pharmaceutical preparation. Examples of these carriers or diluents include starches such as potato starch, wheat starch, corn starch and rice starch; sugars such as lactose, sucrose, glucose, mannitol and sorbitol; celluloses such as crystalline cellulose, carboxy methyl cellulose calcium and hydroxypropyl cellulose of a low degree of substitution; inorganic substances such as potassium phosphate, calcium sulfate, calcium carbonate and talc; binder compounds such as gelatin, gum arabic, methyl cellulose, carboxy methyl cellulose sodium, polyvinyl pyrrolidone and hydroxypropyl cellulose; polyhydric alcohol ester-type nonionic surfactants such as fatty acid monoglycerides, sorbitan fatty acid esters, sucrose and polyglycerol fatty acid esters; and polyoxyethylene-type non-ionic surfactants.

The pharmaceutical composition may be in any known dosage forms known in the art of formulating pharmaceuticals, such as suppositories, powders, granules, tablets, sublingual tablets, liquid preparations, injectable preparations, and suspensions.

The pharmaceutical composition may be administered by any of peroral or parenteral routes, such as intravenous, sublingual or intrarectal administration. For long-term administration, the oral route is preferred.

The dose may be changed as desired. For example, the compound of formula (I) may be administered in a dose of about 1 to about 100 mg/body/day, preferably about 5 to about 50 mg/body/day. The compounds of this invention have extremely low toxicity as shown by their acute toxicity ($LD_{50}$) of 800 to 1500 mg/kg (mouse, oral) and 80 to 120 mg/kg (mouse, intravenous).

The compounds of this invention have shown a significant blood flow increasing action when tested by measuring coronary blood flow using dogs.

The following Examples illustrate the compounds of this invention and methods for their production.

EXAMPLE 1

4-(2-Hydroxy-3-isopropylamino)propoxy-N-(3-nitroxypropyl)benzamide of the formula:

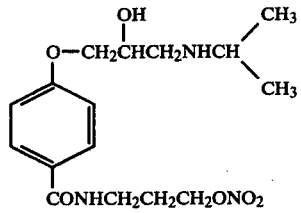

CONHCH₂CH₂CH₂ONO₂

(A) Methyl p-hydroxybenzoate (11.5 g) was added to 17.0 g of 3-aminopropanol, and the mixture was stirred at 120° C. for 8 hours. Then, the reaction mixture was added to 1 N hydrochloric acid and extracted with ethyl acetate. The extract was washed with an aqueous solution of sodium chloride and dried. Evaporation of the solvent gave a crude product. The crude product was purified by silica gel column chromatography to give 9.3 g (yield 63.7%) of 4-hydroxy-N-(3-hydroxypropyl)benzamide.

(B) The resulting benzamide (8.5 g) was added to 42 ml of epichlorohydrin, and 21 ml of piperidine was added. The mixture was stirred at 70° C. for 6 hours. The reaction mixture was purified as above using ethyl acetate to give 4.5 g (yield 41.1%) of 4-(2,3-epoxy)-propoxy-N-(3-hydroxypropyl)benzamide.

(C) The resulting epoxy compound (3.0 g) was dissolved in 100 ml of acetonitrile. The solution was cooled to −20° C., and with stirring, a mixture of 1.84 g of acetic anhydride and 1.13 g of fuming nitric acid were added dropwise. Twenty-five minutes later, the same amount of the mixed acid was added dropwise, and the mixture was stirred. After the reaction, an aqueous solution of sodium hydrogen carbonate and an aqueous solution of sodium chloride were added, and the mixture was extracted with ethyl acetate. The extract was washed with an aqueous solution of sodium chloride and dried. Evaporation of the solvent gave a crude product. The crude product was recrystallized from a mixture of ethyl acetate and n-hexane to give 2.85 g (yield 80.6%) of 4-(2,3-epoxy)propoxy-N-(3-nitroxypropyl)benzamide as colorless needle-like crystals having a melting point of 108° to 110° C. The NMR and IR data of the product were as follows:

NMR: δ(CDCl₃):
1.73–2.27 (2H, m, —NHCH₂C$\underline{H_2}$CH₂ONO₂),
2.60–3.03 (2H, m,

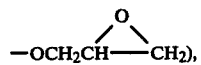

4.47 (2H, t, J=6 Hz, —NHCH₂CH₂C$\underline{H_2}$ONO₂),
6.78 (2H, d, J=9 Hz, H of the aromatic ring),
7.63 (2H, d, J=9Hz, H of the aromatic ring).

IR: $\nu_{max}^{KBr}$ cm⁻¹: 3320 (—CONH—), 1630 (—NO₂), 1260 (—NO₂).

(D) The resulting nitroxy compound (1.20 g) was dissolved in 12 ml of methanol, and 1.37 g of isopropylamine was added. The mixture was refluxed for 30 minutes. The reaction mixture was concentrated and recrystallized from ethyl acetate to give 1.16 g (yield 81.7%) of 4-(2-hydroxy-3-isopropylamino)propoxy-N-(3-nitroxypropyl)benzamide as needle-like crystals having a melting point of 103° to 105° C. The NMR and IR data of the product were as follows:

NMR: δ(CDCl₃—CD₃OD):
1.10 (6H, d, J=6 Hz,

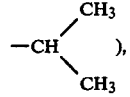

1.75–2.30 (2H, m, —NHCH₂C$\underline{H_2}$CH₂ONO₂),
4.50 (2H, t, J=6 Hz, —NHC$\underline{H_2}$CH₂C$\underline{H_2}$ONO₂),
6.84 (2H, d, J=8 Hz, H of the aromatic ring),
7.68 (2H, d, J=8 Hz, H of the aromatic ring).

IR: $\nu_{max}^{KBR}$ cm⁻¹: 1630 (—NO₂), 1260 (—NO₂).

In the same way as in Example 1, the following compounds were prepared.

EXAMPLE 2

3-(2-Hydroxy-3-isopropylamino)propoxy-N-(3-nitroxypropyl)benzamide of the formula:

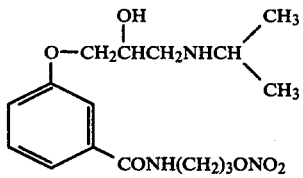

Form: Colorless needle-like crystals.
Melting point: 84°–87° C.
NMR: δ(CDCl$_3$):
1.05 (6H, d, J=6 Hz,

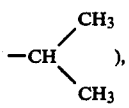

1.75–2.28 (2H, m, —NHCH$_2$CH$_2$CH$_2$ONO$_2$),
4.48 (2H, t, J=6 Hz, —NHCH$_2$CH$_2$CH$_2$ONO$_2$),
6.74–7.24 (4H, m, H of the aromatic ring).
IR: $\nu_{max}^{KBr}$ cm$^{-1}$: 1625 (—NO$_2$), 1280 (—NO$_2$).

EXAMPLE 3

2-(2-Hydroxy-3-isopropylamino)propoxy-N-(2-nitroxyethyl)benzamide of the formula

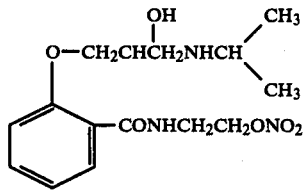

Form: Pale yellow viscous oil.
NMR: δ(CDCl$_3$):
1.10 (6H, d, J=6 Hz,

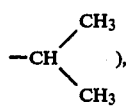

3.70 (2H, t, J=5 Hz, —NHCH$_2$CH$_2$ONO$_2$),
4.55 (2H, t, J=5 Hz, —NHCH$_2$CH$_2$ONO$_2$),
6.70–8.10 (4H, m, H of the aromatic ring).
IR: $\nu_{max}^{KBr}$ cm$^{-1}$: 1630 (—NO$_2$), 1275 (—NO$_2$).

EXAMPLE 4

4-(2-Hydroxy-3-isopropylamino)propoxy-N-(2-nitroxyethyl)benzamide of the formula:

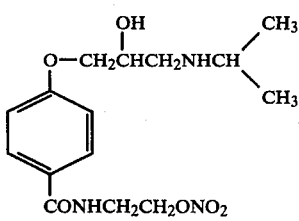

Form: Colorless needle-like crystals.
Melting point: 95°–96° C.
NMR: δ(CDCl$_3$—CD$_3$OD):
1.09 (6H, d, J=6 Hz,

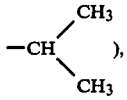

3.65 (2H, t, J=5 Hz, —NHCH$_2$CH$_2$ONO$_2$),
4.57 (2H, t, J=5 Hz, —NHCH$_2$CH$_2$ONO$_2$),
6.82 (2H, d, J=8 Hz, of the aromatic ring),
7.65 (2H, d, J=8 Hz, of the aromatic ring).
IR: $\nu_{max}^{KBr}$ cm$^{-1}$: 1640 (—CONH—), 1620 (—NO$_2$), 1290 (—CONH—), 1260 (—NO$_2$).

What is claimed is:

1. A compound represented by the following formula

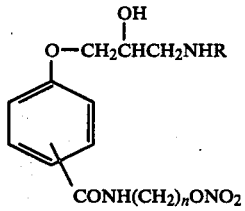

wherein R represents a lower alkyl group having 2 to 6 carbon atoms, and n is an integer of from 1 to 5.

2. The compound of claim 1 wherein R represents a C$_3$ alkyl group.

3. The compound of claim 1 wherein n is 2 or 3.

4. The compound of claim 1 which is a member selected from the group consisting of 4-(2-hydroxy-3-isopropylamino)propoxy-N-(3-nitroxypropyl)benzamide, 3-(2-hydroxy-3-isopropylamino)propoxy-N-(3-nitroxypropyl)benzamide, 2-(2-hydroxy-3-isopropylamino)propoxy-N-(2-nitroxyethyl)benzamide, and 4-(2-hydroxy-3-isopropylamino)propoxy-N-(2-nitroxyethyl)benzamide.

* * * * *